United States Patent
Felder et al.

(10) Patent No.: US 10,080,813 B2
(45) Date of Patent: Sep. 25, 2018

(54) STERILE PACKAGE SYSTEM FOR MEDICAL DEVICE

(75) Inventors: Kevin D. Felder, Cincinnati, OH (US); Michael J. Stokes, Cincinnati, OH (US); Christopher B. Anderson, Oak Grove, MN (US); Frederick E. Shelton, IV, Hillsboro, OH (US); David C. Yates, West Chester, OH (US); John W. Willis, Cincinnati, OH (US); Ashvani K. Madan, Mason, OH (US); Donna L. Korvick, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 1538 days.

(21) Appl. No.: 13/151,515

(22) Filed: Jun. 2, 2011

(65) Prior Publication Data

US 2012/0305427 A1 Dec. 6, 2012

(51) Int. Cl.
*A61L 2/08* (2006.01)
*A61L 2/22* (2006.01)
*A61M 5/00* (2006.01)
*A61L 2/26* (2006.01)
*B65B 55/18* (2006.01)
(Continued)

(52) U.S. Cl.
CPC ............... *A61L 2/22* (2013.01); *A61B 50/30* (2016.02); *A61L 2/26* (2013.01); *A61M 5/002* (2013.01); *A61M 39/18* (2013.01); *B65B 55/18* (2013.01); *A61B 17/07207* (2013.01); *A61B 50/33* (2016.02); *A61B 2017/00362* (2013.01); *A61B 2017/00734* (2013.01); *A61B 2050/0065* (2016.02); *A61B 2050/3008* (2016.02); *A61B 2050/314* (2016.02); *A61L 2202/181* (2013.01);
(Continued)

(58) Field of Classification Search
CPC .... A61L 2/08; B65D 1/32; B65D 1/36; B65D 25/005
USPC ............... 422/28, 26, 22; 220/265, 270, 529
See application file for complete search history.

(56) References Cited

U.S. PATENT DOCUMENTS 3,983,994 A * 10/1976 Wyslotsky ..................... 206/219
4,798,292 A * 1/1989 Hauze ........................... 206/439
(Continued)

FOREIGN PATENT DOCUMENTS

DE 29608617 8/1996
WO WO 98/06144 2/1998

OTHER PUBLICATIONS

"Seal" American Heritage Dictionary of the English Language. Fifth Edition (2011). Houghton Mifflin Harcourt Publishing Company.*
(Continued)

*Primary Examiner* — Donald R Spamer
(74) *Attorney, Agent, or Firm* — Frost Brown Todd LLC (57) ABSTRACT

An apparatus for aseptic insertion includes a container, a first cover, and a second cover. The container includes a first compartment, a second compartment, and a detachable wall disposed between the first compartment and the second compartment. The first cover is sized and configured to attach to the first compartment and the second cover is sized and configured to attach to the container. The detachable wall may defined by a top portion, a portion of a first distal wall of the first compartment, and a portion of a second proximal wall of the second compartment. The detachable wall may be removably attached to the first cover by the top portion of the detachable wall.

17 Claims, 8 Drawing Sheets

(51) Int. Cl.
*A61M 39/18* (2006.01)
*A61B 50/30* (2016.01)
A61B 17/072 (2006.01)
B65B 5/04 (2006.01)
A61B 17/00 (2006.01)
A61B 50/00 (2016.01)
A61B 50/33 (2016.01)

(52) U.S. Cl.
CPC ..... *A61L 2202/182* (2013.01); *A61L 2202/24* (2013.01); *B65B 5/04* (2013.01)

(56) References Cited

U.S. PATENT DOCUMENTS

| | | | |
|---|---|---|---|
| 5,163,557 | A | 11/1992 | Sokolowski |
| 5,168,863 | A | 12/1992 | Kurtzer |
| 5,176,634 | A * | 1/1993 | Smith et al. .............. 604/87 |
| 5,178,282 | A | 1/1993 | Williams |
| 5,792,045 | A | 8/1998 | Adair |
| 5,873,814 | A | 2/1999 | Adair |
| 6,500,176 | B1 | 12/2002 | Truckai et al. |
| 6,589,164 | B1 | 7/2003 | Flaherty |
| 6,622,864 | B1 | 9/2003 | Debbs et al. |
| 7,416,101 | B2 | 8/2008 | Shelton, IV et al. |
| 7,501,198 | B2 | 3/2009 | Barlev et al. |
| 7,578,391 | B2 | 8/2009 | Nakamura |
| 7,738,971 | B2 | 6/2010 | Swayze et al. |
| 2003/0205029 | A1 | 11/2003 | Chapolini et al. |
| 2006/0079874 | A1 | 4/2006 | Faller et al. |
| 2006/0186010 | A1 * | 8/2006 | Warnack et al. ............. 206/438 |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0026216 | A1 * | 1/2009 | Philpott ....................... 220/666 |
| 2009/0209990 | A1 | 8/2009 | Yates et al. |
| 2010/0069940 | A1 | 3/2010 | Miller et al. |

OTHER PUBLICATIONS

International Search Report and Written Opinion dated Jun. 10, 2013 for PCT/US2012/040088.
"System 6 Aseptic Battery System," Stryker Instruments (Jul. 18, 2011) pp. 1-2.
U.S. Appl. No. 13/151,509, filed Jun. 2, 2011, Smith et al.
U.S. Appl. No. 13/176,875, filed Jul. 6, 2011, Smith et al.
U.S. Appl. No. 12/576,776, filed Oct. 9, 2009, Boudreaux et al.
U.S. Appl. No. 13/151,471, filed Jun. 2, 2011, Stulen et al.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,512, filed Jun. 2, 2011, Houser et al.
U.S. Appl. No. 13/151,515, filed Jun. 2, 2011, Felder et al.

* cited by examiner

STERILE PACKAGE SYSTEM FOR MEDICAL DEVICE

BACKGROUND

Packages for medical devices have been made for a variety of medical devices. In general, medical devices may be packaged in a single package with only some corresponding components included within a single container. Such containers may be designed to maintain sterility of the medical device from the time of sterilization until the time for use by a medical professional. These containers may be generally constructed from materials such as plastic, high density polyethylene fiber material (such as Tyvek®), and others. Once packaged, the medical device and package may be sterilized once prior to the use by a medical professional. Such sterilization methods may include gamma radiation, electron beam processing, x-ray radiation, or ultraviolet light irradiation. Some of these methods of sterilization may be incompatible with or cause damage to certain components within a medical device. When this is the case, a separate bulky support device may be provided to connect the medical device for use.

With the advancement of the electronics industry, medical devices may be adapted to contain most, if not all, of the required components within the medical device. More specifically, some medical devices may be adapted to use an internal or attachable power source instead of requiring the device to be plugged into an external source by a cable. Merely exemplary devices that may be adapted to include a portable power source are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2009/0209990 entitled "Motorized Surgical Cutting and Fastening Instrument Having Handle Based Power Source," published Aug. 20, 2009, issued on Feb. 25, 2014 as U.S. Pat. No. 8,657,174, the disclosure of which is incorporated by reference herein; and U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein.

While several systems and methods have been made and used for packaging medical devices, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Medical Devices

Figure 1:
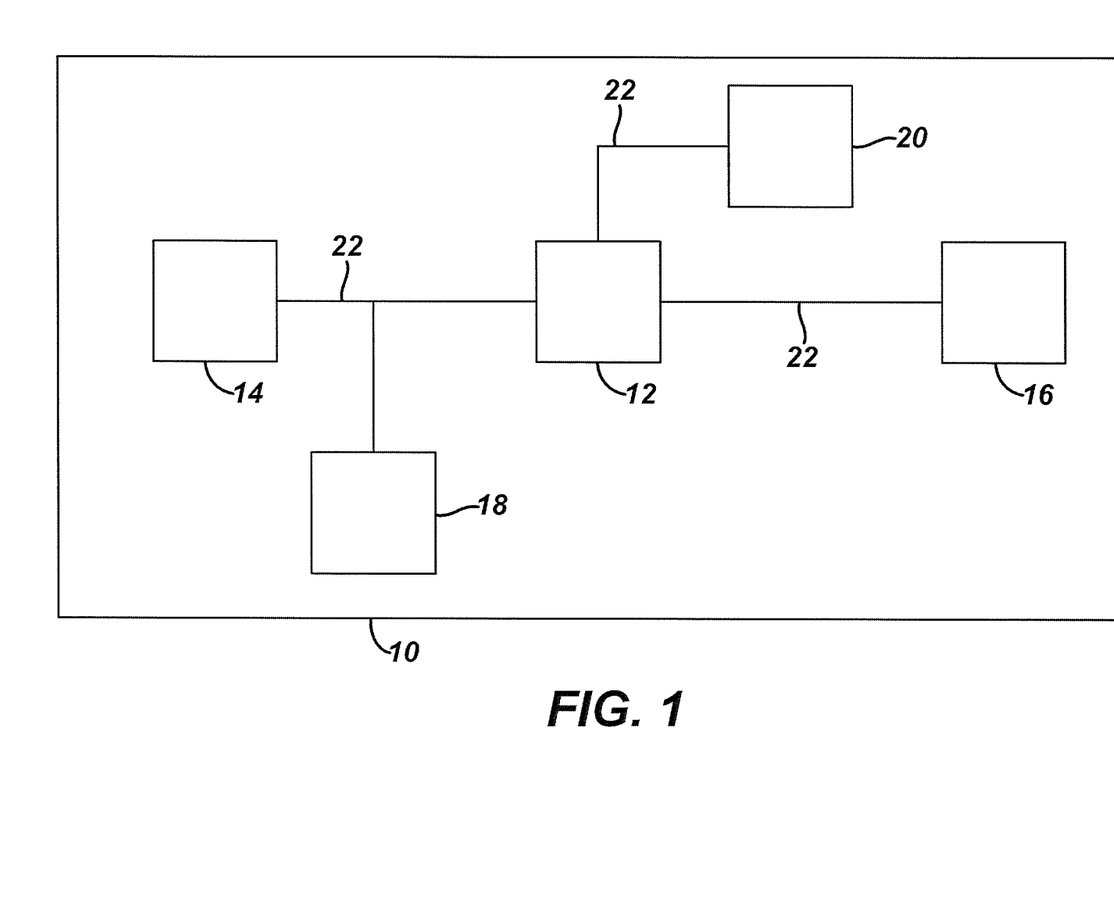
FIG. 1 depicts a schematic view of an exemplary medical device having an internal power source.

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
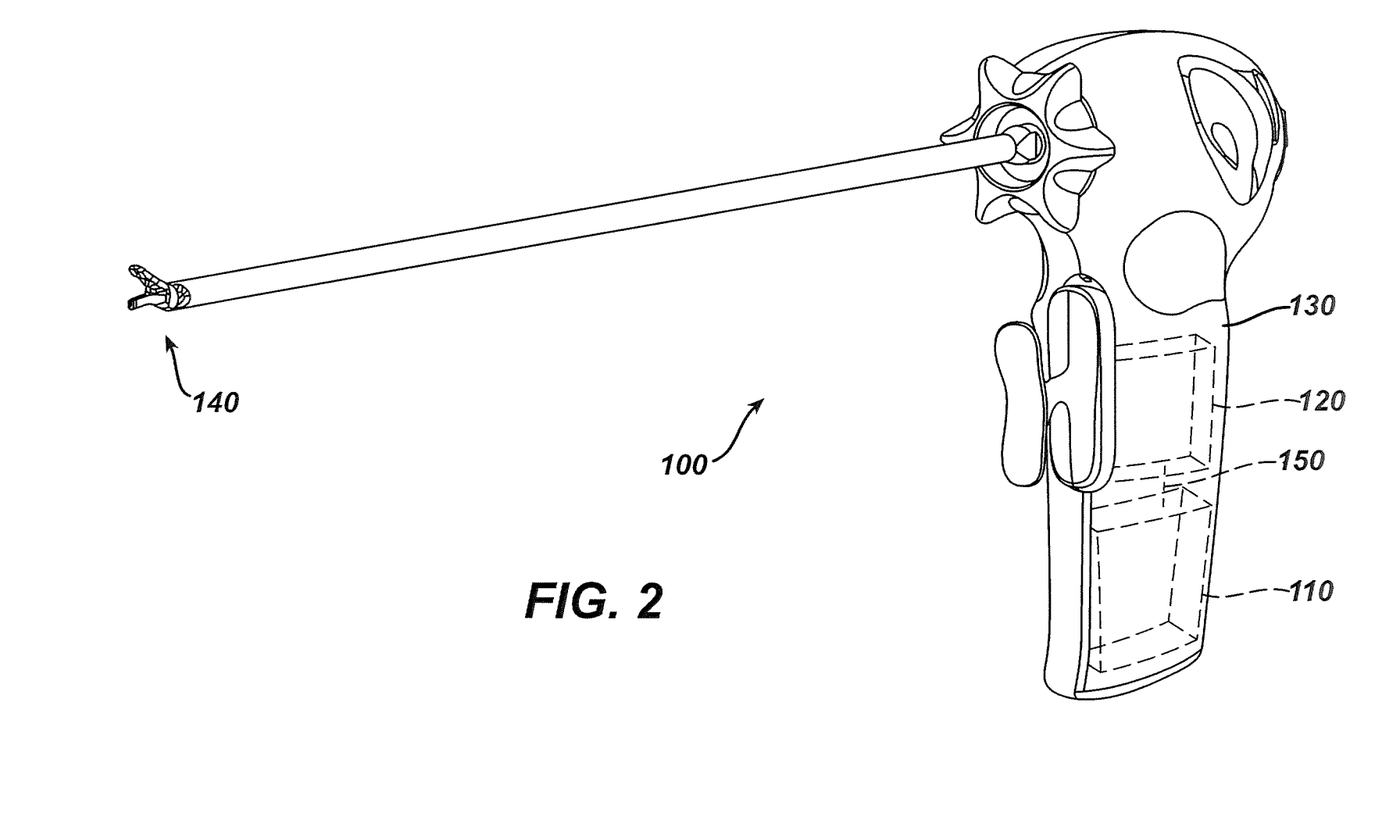
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein. While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. Nos. 6,500,176; 7,416,101; 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, issued as U.S. Pat. No. 8,657,174 on Feb. 25, 2014; U.S. Pub. No. 2010/0069940, now U.S. Pat. No. 9,023,071, issued May 5, 2015; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. patent application Ser. No. 13/151,471, entitled "Medical Device Packaging with Charging Interface", now U.S. Pat. No. 9,000,720, issued on Apr. 7, 2015; U.S. patent application Ser. No., 13/151,481, entitled "Motor Driven Electrosurgical Device with Mechanical and Electrical Feedback"; filed on Jun. 2, 2011, published on May 10, 2012 as U.S. Pub. No. 2012/0116379, now U.S. Pat. No. 9,161,803, issued Oct. 20, 2015; U.S. patent application Ser. No 13/151,488, entitled "Packaging for Reclaimable Component of a Medical Device", filed on Jun. 2, 2011, published on May 10, 2012 as U.S. Pub. No. 2012/0111591; U.S. patent application Ser. No. 13/151,498, entitled "Sterile Housing for Non-Sterile Medical Device Component" filed on Jun. 2, 2011, issued on Apr. 28, 2015 as U.S. Pat. No. 9,017,851; U.S. patent application Ser. No. 13/151,503, entitled "Sterile Medical Instrument Charging Device" filed on Jun. 2, 2011, published on May 10, 2012 as U.S. Pub. No. 2012/0116380, now U.S. Pat. No. 9,597,143, issued Mar. 21, 2017; U.S. patent application Ser. No. 13/151,509, entitled "Medical Device Packaging with Window for Insertion of Reusable Component" filed on Jun. 2, 2011 and published on May 10, 2012 as U.S. Pub. No. 2012/0110824, now U.S. Pat. No. 9,089,338, issued Jul. 28, 2015; and U.S. patent application Ser. No. 13/151,512, entitled "Medical Device with Feature for Sterile Acceptance of Non-31Sterile Reusable Component" published on May 10, 2012 as U.S. Pub. No. 2012/0110810, now U.S. Pat. No. 9,072,523, issued Jul. 7, 2015. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

II. Package Systems for Medical Device with Insertable Electrical Component

For medical devices utilizing specialized components, such as electrical components or other sensitive components, certain forms of sterilization may damage those components if the fully assembled medical device undergoes that sterilization. However, if an alternative sterilization method is used on the fully assembled device to avoid damaging the inserted components, it is possible that portions of the medical device will not be sterilized. Accordingly, it may be advantageous to treat the medical device without those insertable components separately by one sterilization method, and then to treat the insertable components by a different sterilization method. It may further be useful to contain both the medical device and the insertable components within a single container or package for convenience.

The following examples relate to various illustrative ways to package insertable electrical components with medical devices such that multiple sterilization methods may be employed to both properly sterilize the medical devices while not substantially damaging the insertable electrical components.

Figure 3:
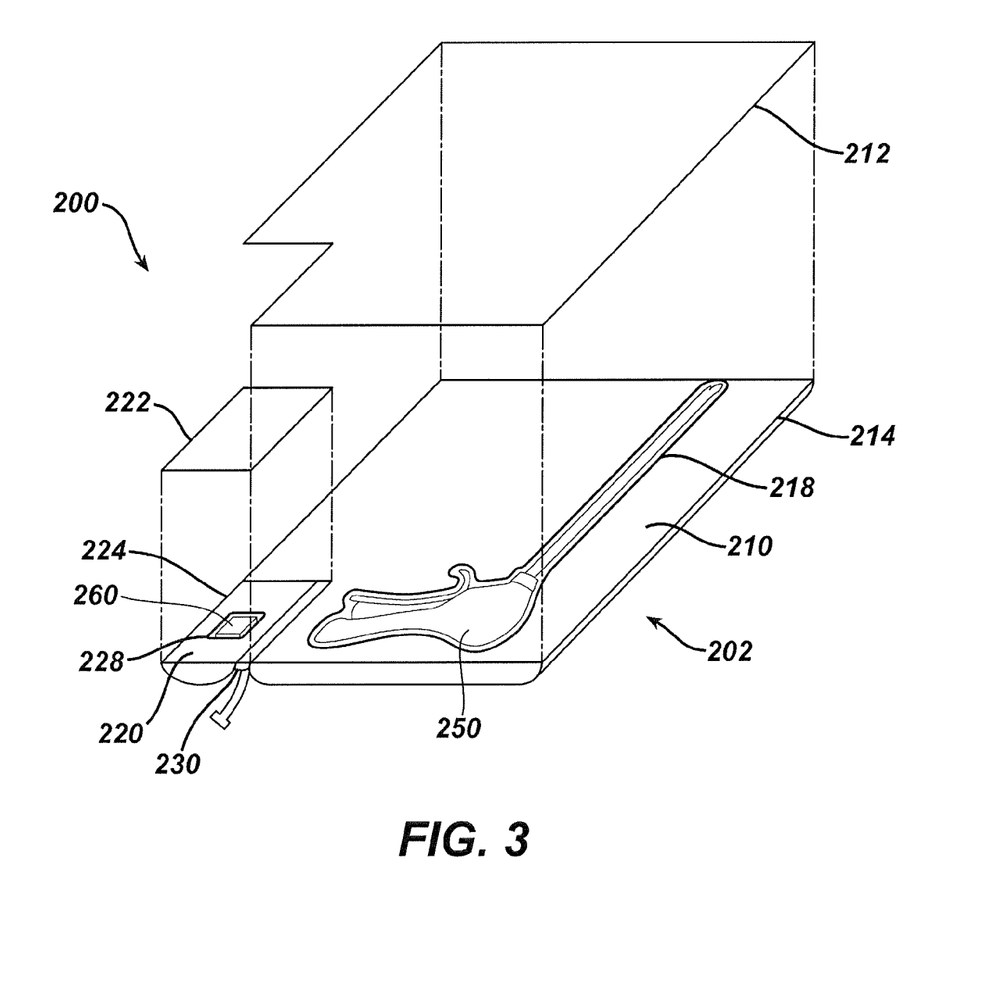
FIG. 3 depicts an exploded perspective view of an exemplary package system for a medical device and an insertable electrical component.

FIG. 3 depicts an exemplary package system (200) comprising a container (202), a first cover (212), and a second cover (222). Container (202) of this example comprises a first compartment (210) and a second compartment (220). Container (202) may be made from a variety of materials including plastics, plastic film, high density polyethylene fiber materials (such as Tyvek®), or any other suitable material to maintain sterility. In the present example, container (202) is a blister tray having first compartment (210) and second compartment (220). In an exemplary configuration depicted in FIG. 3, first compartment (210) may be separated from second compartment (220) by a detachable wall (230), as will be later described in more detail regarding insertion assembly (500).

First compartment (210) is sized to contain a medical device (250) therein. By way of example only, medical device (250) may be constructed in accordance with at least some of the teachings of medical device (10) or medical device (100) as previously referred to herein or medical device (250) may have any other suitable configuration as will be apparent to one of ordinary skill in the art in view of the teachings herein. In the present example, first compartment (210) has a first recess (218) sized to the profile of medical device (250) such that medical device (250) is substantially restrained within first compartment (210). Alternatively, first compartment (210) may be a heat-shrunk compartment. Further still, first compartment (210) may be substantially open, allowing medical device (250) to be substantially unrestrained within first compartment (210) or medical device (250) may be held in place by bosses (not shown). One such example of an open compartment may include a simple rigid compartment. First compartment (210) may also contain other accessories for use with medical device (250). First compartment (210) may include additional recesses to fit the profiles of these various accessories. Alternatively, if first compartment (210) is substantially open, these accessories may include their own sub-packaging, such as cardboard boxes, to keep the accessories separate within first compartment (210). Various other suitable ways to configure first compartment (210) to contain medical device (250) will be apparent to those of ordinary skill in the art in view of the teachings herein.

First cover (212) is sized to conform to the size of first compartment (210). First cover (212) has a portion removed that corresponds to the size of second compartment (220) such that first cover (212) does not overlap second compartment (220), though it should be noted that the removed portion is merely optional and first cover (212) may be sized to overlap a portion or the entire second compartment (220). First cover (212) may be made from a variety of materials including plastics, plastic peelable films, high density polyethylene fiber materials (such as Tyvek®), or any other suitable material to maintain sterility. First cover (212) is configured to attach to and seal first compartment (210). By way of example only, first cover (212) may be attached by adhesive, such as cyanoacrylate or epoxy, on a first rim (214) of first compartment (210). Alternatively, first cover (212) may be configured to snap on to first rim (214) of first compartment (210). In yet a further exemplary configuration, first cover (212) may be heat sealed to first rim (214) of first compartment (210). Various other materials for first cover (212) and other suitable ways to attach first cover (212) to first compartment (210) will be apparent to those of ordinary skill in the art in view of the teachings herein.

Second compartment (220) is sized to contain an insertable electrical component (260) therein. By way of example only, insertable electrical component (260) may comprise a power source, such as one of the types of batteries previously discussed herein, a plurality of batteries in the form of a battery pack, a printed circuit board, a transducer, and/or any other insertable component or combination of components as will be apparent to those of ordinary skill in the art in view of the teachings herein. Second compartment (220) has a second recess (228) sized to the profile of insertable electrical component (260) such that insertable electrical component (260) is substantially restrained within second compartment (220). Second compartment (220) may alternatively be a heat-shrunk compartment. Yet a further alternative is for second compartment (220) to be substantially open, allowing insertable electrical component (260) to be substantially unrestrained within second compartment (220) or retained only by bosses (not shown). One such exemplary open compartment may be a simple rigid compartment. Various other suitable ways to configure second compartment (220) to contain insertable electrical component (260) may be provided as will be apparent to those of ordinary skill in the art in view of the teachings herein.

Second cover (222) is sized to conform to the size of second compartment (220), though it should be noted that second cover (222) may be alternatively sized to cover both second compartment (220) and a portion or the entirety of first compartment (212) as will be discussed in more detail herein regarding second cover (322). Second cover (222) may be made from a variety of materials including plastics, plastic peelable films, high density polyethylene fiber materials (such as Tyvek®), or any other suitable material to maintain sterility. Second cover (222) is configured to attach to and seal second compartment (220). By way of example only, second cover (222) may be attached by adhesive, such as cyanoacrylate or epoxy, on a second rim (224) of second compartment (220). Alternatively, second cover (222) may be configured to snap on to second rim (224) of second compartment (220). In yet a further exemplary configuration, second cover (222) may be heat sealed to second rim (224) of second compartment (220). Various other materials for second cover (222) and other suitable ways to attach second cover (222) to second compartment (220) will be apparent to those of ordinary skill in the art in view of the teachings herein.

One exemplary implementation of package system (200) is for dual sterilization. Medical device (250) is first inserted into first compartment (210) of container (202). First cover (212) is then attached to and seals first compartment (210). Container (202), medical device (250), and first cover (212) may then be sterilized by a first sterilization method. In one exemplary sterilization technique, container (202) is placed in a field of radiation that can penetrate container (202), such as gamma radiation, x-rays, or high-energy electrons. The radiation may kill bacteria on medical device (250) and within first compartment (210) of container (202). Container (202) may also be sterilized using any other technique known in the art, including but not limited to beta or gamma radiation, ethylene oxide, electron beam sterilization, or steam. Subsequently, insertable electrical component (260) is then inserted into second compartment (220) of container (202). Second cover (222) is then attached to and seals second compartment (220). Package system (200), comprising container (202), medical device (250), insertable electrical component (260), first cover (212), and second cover (222), may then be sterilized by a second sterilization method. One such second sterilization method is electron beam sterilization for surface sterilization, though it should be understood that other sterilization methods may also be employed. Furthermore, while the second sterilization method is described as applying to the whole package system (200), the second sterilization method may be applied to individual portions of package system (200), such as insertable electrical component (260) or second cover (222), or the second sterilization method may be applied to any combination of portions of package system (200), such as insertable electrical component (260), second compartment (220), and/or second cover (222). While one exemplary implementation of package system (200) has been described, various other implementations of package system (200) will be apparent to those of ordinary skill in the art in view of the teachings herein. Additionally, while only certain sterilization methods have been described, various other suitable first and second sterilizations may be provided that will be apparent to those of ordinary skill in the art in view of the teachings herein.

Figure 4:
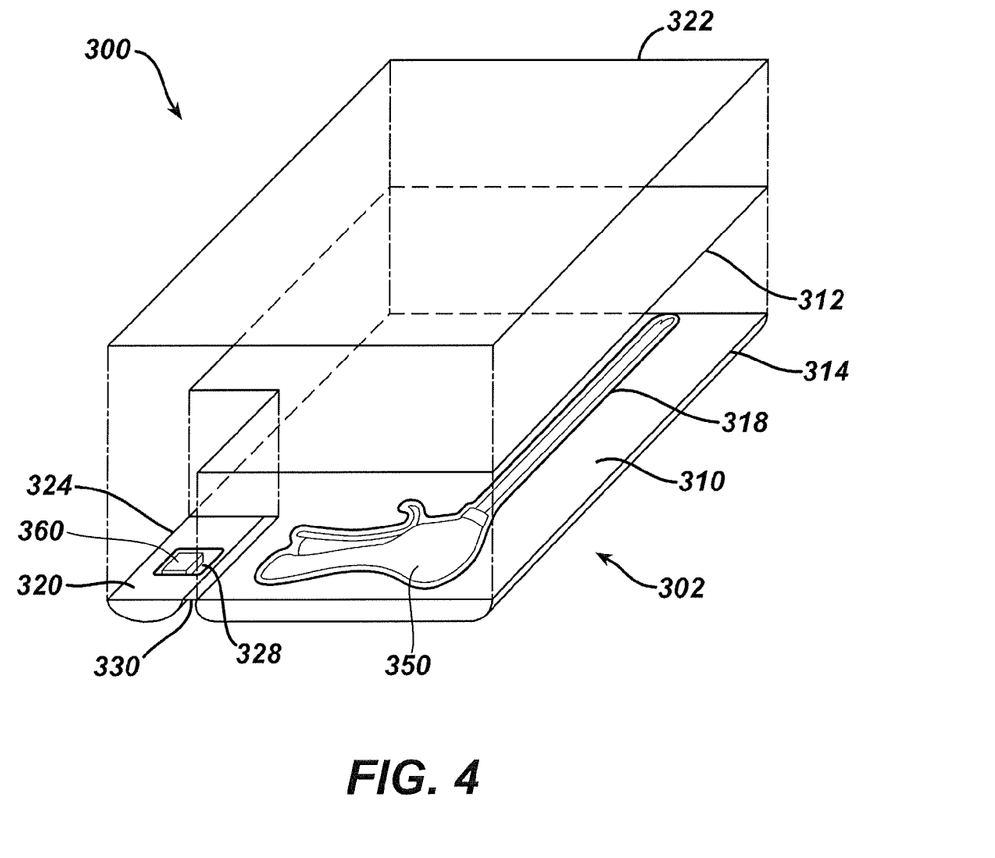
FIG. 4 depicts an exploded perspective view of another example of an exemplary package system for a medical device and an insertable electrical component.

FIG. 4 depicts one alternative exemplary package system (300) comprising a container (302), a first cover (312), and a second cover (322). Container (302) of this example comprises a first compartment (310) and a second compartment (320). Container (302) may be made from a variety of materials including plastics, high density polyethylene (such as Tyvek®), or any other suitable material to maintain sterility. In the present example, container (302) is a blister tray having first compartment (310) and second compartment (320). In an exemplary configuration depicted in FIG. 4, first compartment (310) may be separated from second compartment (320) by a detachable wall (330), as will be later described in more detail regarding insertion assembly (500).

First compartment (310) is sized to contain a medical device (350) therein. By way of example only, medical device (350) may be constructed in accordance with at least some of the teachings of medical device (10), medical device (100), or medical device (250) as previously referred to herein or medical device (350) may have any other suitable configuration as will be apparent to one of ordinary skill in the art in view of the teachings herein. In the present example, first compartment (310) has a first recess (318) sized to the profile of medical device (350) such that medical device (350) is substantially restrained within first compartment (310). An alternative first compartment (310) may be a heat-shrunk compartment. First compartment (310) may instead be substantially open, allowing medical device (350) to be substantially unrestrained within first compartment (310) or only held in place by bosses (not shown). One such exemplary open compartment may include a simple rigid compartment. First compartment (310) may also contain other accessories for use with medical device (350). First compartment (310) may include additional recesses to fit the profiles of these various accessories. Alternatively, if first compartment (310) is substantially open, these accessories may include their own sub-packaging, such as cardboard boxes, to keep the accessories separate within first compartment (310). Various other suitable ways to configure first compartment (310) to contain medical device (350) will be apparent to those of ordinary skill in the art in view of the teachings herein.

First cover (312) is sized to conform to the size of first compartment (310). First cover (312) has a portion removed that corresponds to the size of second compartment (320) such that first cover (312) does not overlap second compartment (320), though it should be noted that the removed portion is merely optional and first cover (312) may be sized to overlap a portion or the entire second compartment (320). First cover (312) may be made from a variety of materials including plastics, plastic peelable film, high density polyethylene fiber materials (such as Tyvek®), or any other suitable material to maintain sterility. First cover (312) is configured to attach to and seal first compartment (310). By way of example only, first cover (312) may be attached by adhesive, such as cyanoacrylate or epoxy, on a first rim (314) of first compartment (310). Alternatively, first cover (312) may be configured to snap on to first rim (314) of first compartment (310). In yet a further exemplary configuration, first cover (312) may be heat sealed to first rim (314) of first compartment (310). Various other materials for first cover (312) and other suitable ways to attach first cover (312) to first compartment (310) will be apparent to those of ordinary skill in the art in view of the teachings herein.

Second compartment (320) is sized to contain an insertable electrical component (360) therein. By way of example only, insertable electrical component (360) may comprise a power source, such as one of the types of batteries previously discussed herein, a plurality of batteries in the form of a battery pack, a printed circuit board, a transducer, and/or any other insertable component or combination of components as will be apparent to those of ordinary skill in the art in view of the teachings herein. Second compartment (320) has a second recess (328) sized to the profile of insertable electrical component (360) such that insertable electrical component (360) is substantially restrained within second compartment (320). An alternative second compartment (320) may be a heat-shrunk compartment. Yet another second compartment (320) may be one that is substantially open, allowing insertable electrical component (360) to be substantially unrestrained within second compartment (320) or secured only by bosses (not shown). One such exemplary open compartment may be a simple rigid compartment. Various other suitable ways to configure second compartment (320) to contain insertable electrical component (360) may be provided as will be apparent to those of ordinary skill in the art in view of the teachings herein.

Second cover (322) is sized to conform to the size of container (302), thereby covering both second compartment (320) and first compartment (310). Second cover (322) may be made from a variety of materials including plastics, plastic peelable film, high density polyethylene fiber materials (such as Tyvek®), or any other suitable material to maintain sterility. Second cover (322) is configured to attach to and seal container (302). By way of example only, second cover (322) may be attached by adhesive, such as cyanoacrylate or epoxy, to a portion of a second rim (324) of second compartment (320) and to a portion of first cover (312). Alternatively, second cover (322) may be configured to snap on to a portion of second rim (324) of second compartment (320) and a portion of first cover (312). In yet a further exemplary configuration, second cover (322) may be heat sealed to a portion of second rim (324) of second compartment (320) and a portion of first cover (312). Various other materials for second cover (322) and other suitable ways to attach second cover (322) to container (302) will be apparent to those of ordinary skill in the art in view of the teachings herein.

One exemplary implementation of package system (300) is for dual sterilization. First, medical device (350) is inserted into first compartment (310) of container (302). First cover (312) is then attached to and seals first compartment (310). Container (302), medical device (350), and first cover (312) may then be sterilized by a first sterilization method. In one exemplary sterilization technique, container (302) is placed in a field of radiation that can penetrate container (302), such as gamma radiation, x-rays, or high-energy electrons. The radiation may kill bacteria on medical device (350) and within first compartment (310) of container (302). Container (302) may also be sterilized using any other technique known in the art, including but not limited to beta or gamma radiation, ethylene oxide, electron beam sterilization, or steam. Subsequently, insertable electrical component (360) is then inserted into second compartment (320) of container (302). Second cover (322) is then attached to a portion of second rim (324) of second compartment (320) and to a portion of first cover (312), thereby sealing container (302). Package system (300), comprising container (302), medical device (350), insertable electrical component (360), first cover (312), and second cover (322), may then be sterilized by a second sterilization method. One such second sterilization method is electron beam sterilization for surface sterilization, though it should be understood that other sterilization methods may also be employed. Furthermore, while the second sterilization method is described as applying to the whole package system (300), the second sterilization method may be applied to individual portions of package system (300), such as insertable electrical component (360) or second cover (322), or the second sterilization method may be applied to any combination of portions of package system (300), such as insertable electrical component (360), second compartment (320), and/or second cover (322). While one exemplary implementation of package system (300) has been described, various other implementations of package system (300) will be apparent to those of ordinary skill in the art in view of the teachings herein. Additionally, while only certain sterilization methods have been described, various other suitable first and second sterilizations may be provided that will be apparent to those of ordinary skill in the art in view of the teachings herein.

Figure 5:
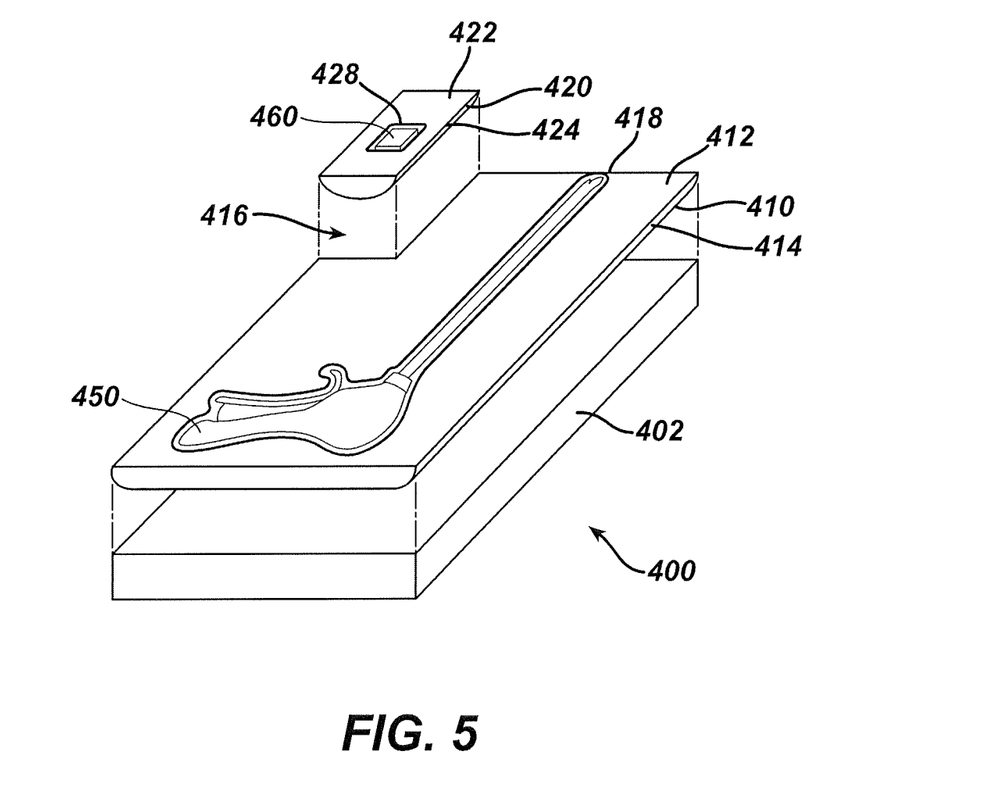
FIG. 5 depicts an exploded perspective view of yet another example of an exemplary package system for a medical device and an insertable electrical component.

FIG. 5 depicts yet a third exemplary package system (400) comprising a box (402), a first container (410), a first cover (412), a second container (420), and a second cover (422). Box (402) is sized to fit both first container (410) and second container (420) when both first container (410) and second container (420) are placed within box (402). Box (402) may be constructed out of a variety of materials, one such example being cardboard.

First container (410) is sized to contain a medical device (450) therein. By way of example only, medical device (450) may be constructed in accordance with at least some of the teachings of medical device (10), medical device (100), medical device (250), or medical device (350) as previously referred to herein or medical device (450) may have any other suitable configuration as will be apparent to one of ordinary skill in the art in view of the teachings herein. In the present example, first container (410) has a first recess (418) sized to the profile of medical device (450) such that medical device (450) is substantially restrained within first container (410). First container (410) of the current example is shown as a blister tray having first recess (418). One alternative first container (410) may be a heat-shrunk container with a rigid first rim (414). Still yet another first container (410) may be one that is substantially open, allowing medical device (450) to be substantially unrestrained within first container (410) or held in place only by bosses (not shown). One such exemplary open container may be a simple rigid container. First container (410) may also contain other accessories for use with medical device (450). First container (410) may include additional recesses to fit the profiles of these various accessories. Alternatively, if first container (410) is substantially open, these accessories may include their own sub-packaging, such as cardboard boxes, to keep the accessories separate within first container (410). First container (410) may also be configured to have a cut-out portion (416). Cut-out portion (416) is sized such that when first container (410) and second container (420), as will be described later herein, are placed within box (402), second container (420) fits within cut-out portion (416) of first container (410), though it should be understood that cut-out portion (416) may be larger than second container (420) or cut-out portion (416) may overlap a portion of second container (420). Various other suitable ways to configure first container (410)

to contain medical device (450) will be apparent to those of ordinary skill in the art in view of the teachings herein.

First cover (412) is sized to conform to the size of first container (410). First cover (412) may be made from a variety of materials including plastics, plastic peelable film, high density polyethylene fiber materials (such as Tyvek®), or any other suitable material to maintain sterility. First cover (412) is configured to attach to and seal first container (410). By way of example only, first cover (412) may be attached by adhesive, such as cyanoacrylate or epoxy, on first rim (414) of first container (410). Alternatively, first cover (412) may be configured to snap on to first rim (414) of first container (410). In yet a further exemplary configuration, first cover (412) may be heat sealed to first rim (414) of first container (410). Various other materials for first cover (412) and other suitable ways to attach first cover (412) to first container (410) may be provided as will be apparent to those of ordinary skill in the art in view of the teachings herein.

Second container (420) is sized to contain an insertable electrical component (460) therein. By way of example only, insertable electrical component (460) may comprise a power source, such as one of the types of batteries previously discussed herein, a plurality of batteries in the form of a battery pack, a printed circuit board, a transducer, and/or any other insertable component or combination of components as will be apparent to those of ordinary skill in the art in view of the teachings herein. Second container (420) has a second recess (428) sized to the profile of insertable electrical component (460) such that insertable electrical component (460) is substantially restrained within second container (420). In the present example, second container (420) is a blister tray having a second recess (428). One alternative second container (420) may be a heat-shrunk container with a rigid second rim (424). Another exemplary second container (420) may be substantially open, allowing insertable electrical component (460) to be substantially unrestrained within second container (420) or held in place only by bosses (not shown). One such exemplary open container may be a simple rigid container. Various other suitable ways to configure second container (420) to contain insertable electrical component (460) will be apparent to those of ordinary skill in the art in view of the teachings herein.

Second cover (422) is sized to conform to the size of second container (420). Second cover (422) may be made from a variety of materials including plastics, plastic peelable film, high density polyethylene fiber materials (such as Tyvek®), or any other suitable material to maintain sterility. Second cover (422) is configured to attach to and seal second container (420). By way of example only, second cover (422) may be attached by adhesive, such as cyanoacrylate or epoxy, to second rim (424) of second container (420). Alternatively, second cover (422) may be configured to snap on to second rim (424) of second container (420). In yet a further exemplary configuration, second cover (422) may be heat sealed to second rim (424) of second container (420). Various other materials for second cover (422) and other suitable ways to attach second cover (422) to second compartment (420) may be provided as will be apparent to those of ordinary skill in the art in view of the teachings herein.

One exemplary implementation of package system (400) is for dual sterilization. First, medical device (450) is inserted into first container (410). First cover (412) is then attached to and seals first container (410). First container (410), medical device (450), and first cover (412) may then be sterilized by a first sterilization method. In one exemplary sterilization technique, first container (410) is placed in a field of radiation that can penetrate first container (410), such as gamma radiation, x-rays, or high-energy electrons. The radiation may kill bacteria on medical device (450) and within first container (410). First container (410) may also be sterilized using any other technique known in the art, including but not limited to beta or gamma radiation, ethylene oxide, electron beam sterilization, or steam. Insertable electrical component (460) is then inserted into second container (420). Second cover (422) is then attached to and seals second container (420). Second container (420), second cover (422), and insertable electrical component (460) may then be sterilized by a second sterilization method. One such second sterilization method is electron beam sterilization for surface sterilization, though it should be understood that other sterilization methods may also be employed. Furthermore, while the second sterilization method is described as applying to the whole second container (420), the second sterilization method may be applied to individual portions of second container (420), such as insertable electrical component (460), empty second container (420), or second cover (422), or to any combination thereof. Second container (420) and first container (410) are then inserted into box (402). Alternatively, first container (410) may be placed within box (402) prior to sterilization. Box (402) containing first container (410) may then undergo the first sterilization method. Second container (420) may then be placed in box (402). Box (402) containing first container (410) and second container (420) may then undergo the second sterilization method. While one exemplary implementation of package system (400) has been described, various other implementations of package system (400) will be apparent to those of ordinary skill in the art in view of the teachings herein. Additionally, while only certain sterilization methods have been described, various other suitable first and second sterilizations may be provided that will be apparent to those of ordinary skill in the art in view of the teachings herein.

While various configurations of exemplary package systems have been described, various other ways in which the package systems may be configured will be apparent to those of ordinary skill in the art in view of the teachings herein. This may include, but is not limited to, implementing a feature from one described exemplary package system with a different exemplary package system described herein.

III. Component Insertion While Maintaining Sterility

If insertable electrical components are contained in separate compartments of a package system, such as in package system (200) or package system (300) as previously described herein, it may be desirable to permit transfer from one compartment to a different compartment while maintaining a substantially sterile field within the container. This may be particularly desirable when insertable electrical components are stored in different compartments of a package system to permit the insertable electrical components to be coupled to a medical device in a different compartment. Accordingly, the following example relates to an illustrative way to permit aseptic transfer from one compartment to a different compartment within the package system.

Figure 6A:
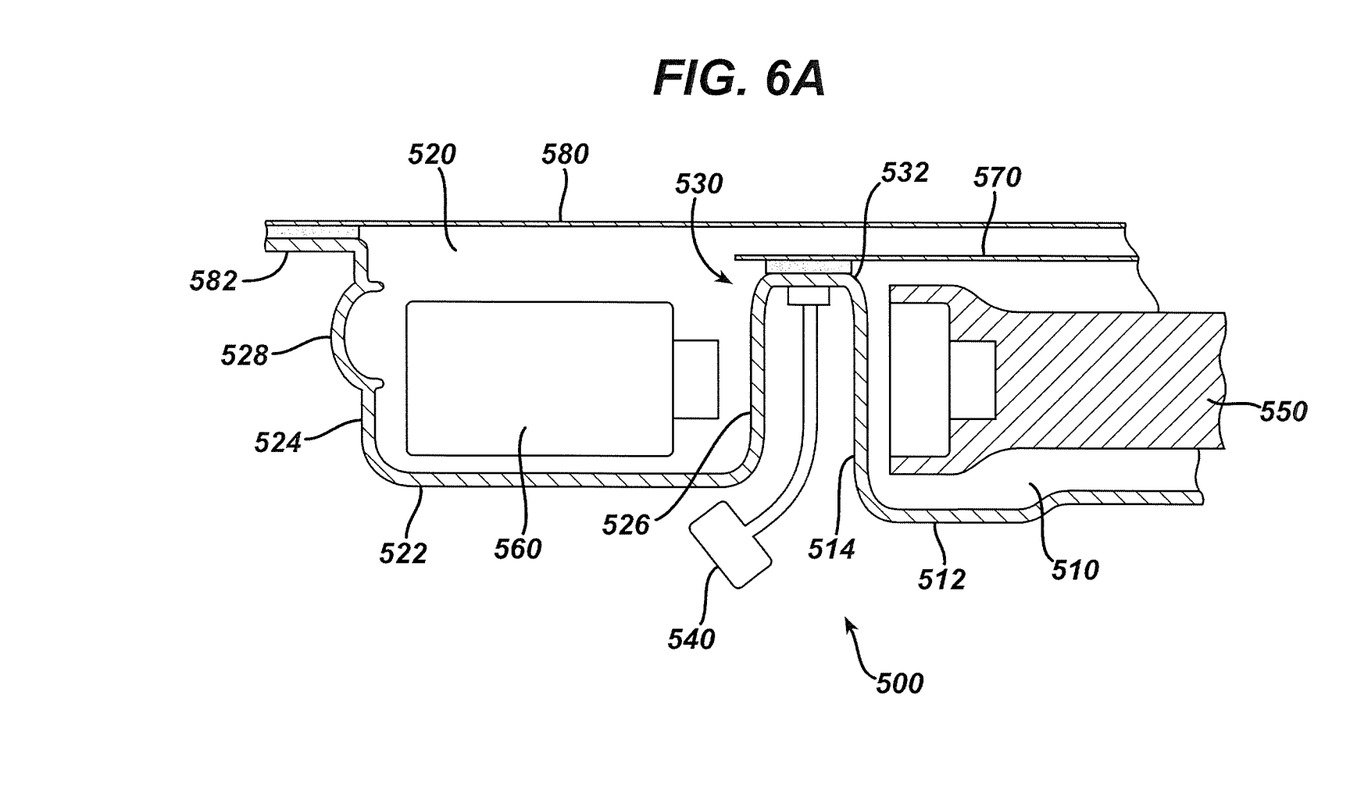
FIG. 6A depicts a partial side cross-sectional view of an example of an exemplary package system showing the insertable electrical component, the medical device, and the release mechanism.
Figure 6B:
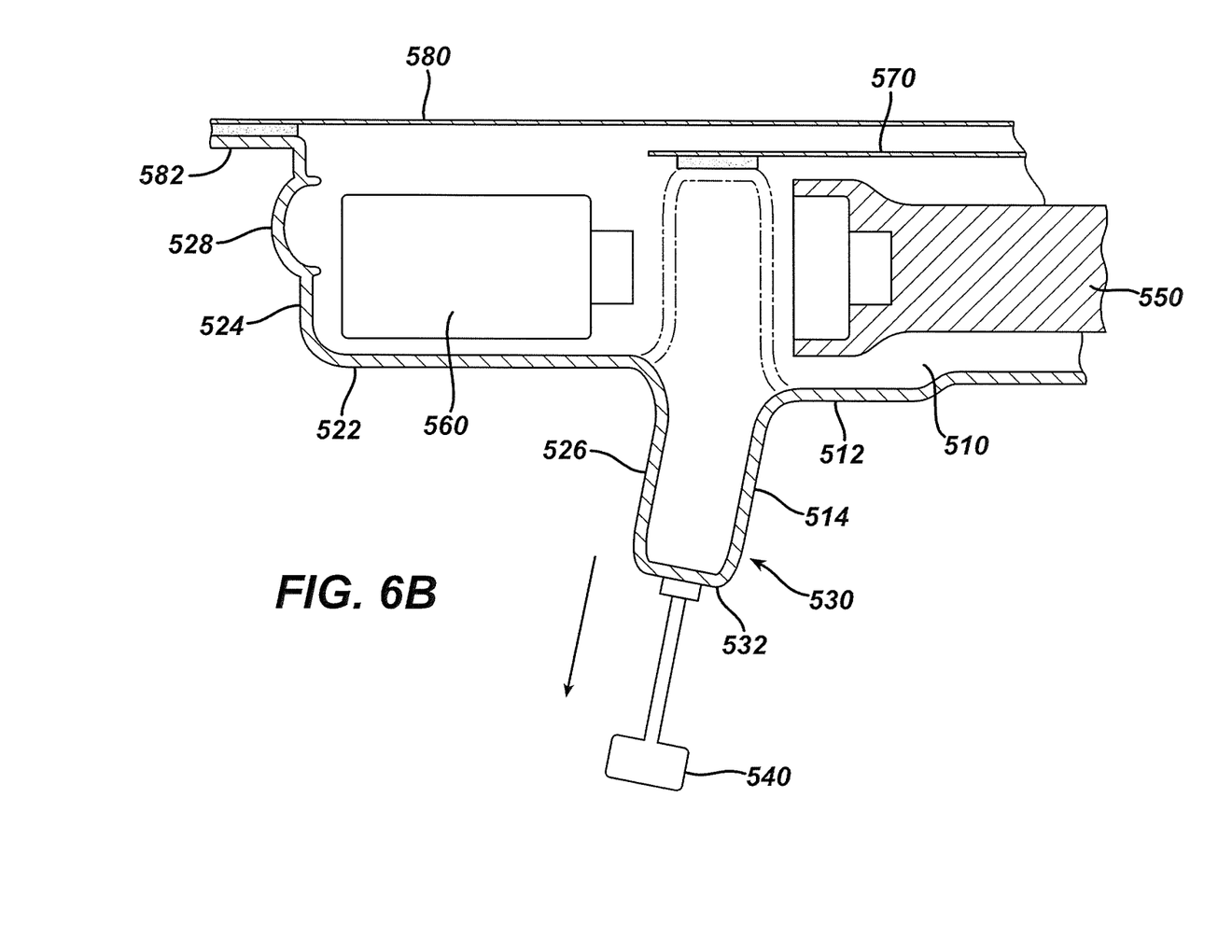
FIG. 6B depicts a partial cross-sectional view of the package system of FIG. 6A, showing the release mechanism in a released position.
Figure 6C:
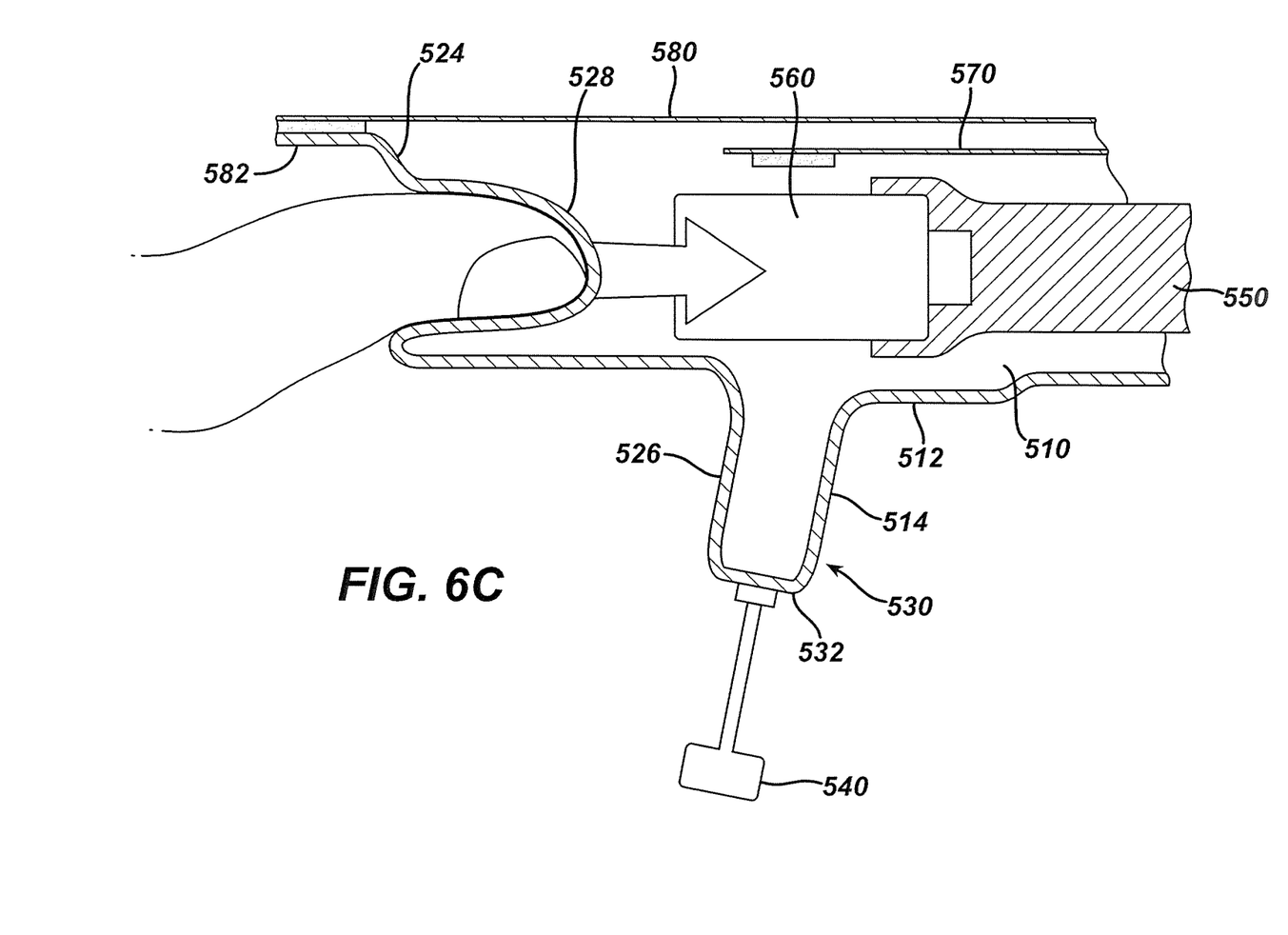
FIG. 6C depicts a partial cross-sectional view of the package system of FIG. 6A, showing the insertion of the insertable electrical component into the medical device.

FIGS. 6A-6C depict an exemplary insertion assembly (500) for a package system. By way of example only, insertion assembly (500) may be readily incorporated into package system (200) of FIG. 3, package system (300) of FIG. 4, or any other suitable package system. A portion of one such exemplary container comprises a first compartment (510), a second compartment (520), and a perimeter rim (582), as shown in FIG. 6A. Perimeter rim (582) of the present example encircles the perimeter of the entire package system and extends outwardly from and perpendicular to perimeter walls (524). While insertion assembly (500) is described in reference to a certain exemplary configuration, insertion assembly (500) may be implemented with a variety of package systems as will be apparent to one of ordinary skill in the art in view of the teachings herein. It should also be understood that multiple insertion assemblies (500) may be implemented with a single package system.

In the present example, first compartment (510) is sized to contain a medical device (550) and is defined by a first distal wall (514), a first bottom surface (512), a first proximal wall (not shown), and sidewalls (not shown). By way of example only, medical device (550) may be constructed in accordance with at least some of the teachings of medical devices (10), (100), (250), (350), or (450) as previously referred to herein or medical device (550) may have any other suitable configuration as will be apparent to one of ordinary skill in the art in view of the teachings herein. Second compartment (520) is sized to contain an insertable electrical component (560) and is defined by a second distal wall (524), a second bottom surface (522), a second proximal wall (526) and sidewalls (not shown). By way of example only, insertable electrical component (560) may comprise a power source, such as one of the types of batteries previously discussed herein, a plurality of batteries in the form of a battery pack, a printed circuit board, a transducer, and/or any other insertable component or combination of components as will be apparent to those of ordinary skill in the art in view of the teachings herein. Both first compartment (510) and second compartment (520) may be made out of a flexible material, such as a plastic, plastic peelable film, a high density polyethylene fiber material (an example of which is Tyvek®), or C-Film by Integra Plastics Inc. of Madison, S. Dak. Alternatively, first distal wall (514) and second compartment (520) may be made of a flexible material while the remainder of first compartment (510), comprising the first bottom surface (512), first proximal wall (not shown) and sidewalls (not shown), may be made of a rigid or semi-rigid material. Various other suitable materials may be used for first compartment (510) or second compartment (520) and will be apparent to those of ordinary skill in the art in view of the teachings herein.

A detachable wall (530) separates first compartment (510) and second compartment (520), thereby keeping insertable electrical component (560) separated from medical device (550). One merely exemplary result is that inadvertent electrical discharge may be limited. Detachable wall (530) is defined by first distal wall (514), second proximal wall (526), and a top portion (532) that extends from first distal wall (514) to second proximal wall (526). A pull tab (540) is attached to detachable wall (530). In the present example, the attachment point of pull tab (540) is on the bottom of top portion (532). Alternatively, pull tab (540) may be attached to a portion of second proximal wall (526), to a portion of first distal wall (514), or to any other suitable attachment point as will be apparent to one of skill in the art in view of the teachings herein. Suitable attachment methods for pull tab (540) may include adhesives, mechanical linkages, or any other suitable attachment methods that will be apparent to one of ordinary skill in the art in light of the teachings herein.

Once medical device (550) is inserted into first compartment (510), a first cover (570) is then attached to seal first compartment (510). First cover (570) may be made from a variety of materials including plastics, plastic peelable film, high density polyethylene fiber materials (such as Tyvek®), or any other suitable material to maintain sterility. In the present example, first cover (570) is attached to top portion (532) and a portion of perimeter rim (582). Alternatively, an interior rim (not shown) may be provided within first compartment (510) as a simple stepped-down portion located inside of perimeter rim (582). First cover (570) may then be attached to top portion (532) and interior rim (not shown). By way of example only, first cover (570) may be attached by an adhesive, such as cyanoacrylate or epoxy, to effectively seal first compartment (510). First cover (570) may alternatively be attached by heat sealing. While a certain materials and attachment methods for first cover (570) have been described herein, various other materials and attachment methods for first cover (570) will be apparent to those of ordinary skill in the art in view of the teachings herein.

After first cover (570) is attached, medical device (550), first cover (570), first compartment (510), and second compartment (520) may then be sterilized by a first sterilization method. In one exemplary sterilization technique, the entire package system is placed in a field of radiation that can penetrate first compartment (510), medical device (550), first cover (570), and second compartment (520), such as gamma radiation, x-rays, or high-energy electrons. The radiation may kill bacteria on medical device (550), within first compartment (510), and within second compartment (520). Alternatively, the entire package system may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein.

Following the first sterilization, insertable electrical component (560) may then be inserted into second compartment (520). If insertable electrical component (560) is a portable battery pack, at the time of insertion the portable battery pack may be fully charged for use with medical device (550). After insertion of insertable electrical component (560) into second compartment (520), a second cover (580) may be attached. Second cover (580) may be sized to cover both second compartment (520) and first compartment (510). For instance, second lid (580) may be constructed similar to second lid (320) described above; or second lid (580) may have any other suitable construction. Alternatively, second cover (580) may be sized to only cover second compartment (520) as shown in FIG. 3. Second cover (580) may be made from a variety of materials including plastics, plastic peelable film, high density polyethylene fiber materials (such as Tyvek®), or any other suitable material to maintain sterility. Second cover (580) of the present example is then attached to perimeter rim (582). Alternatively, second cover (580) may be attached to a portion of perimeter rim (582) and to a portion of first cover (570). Second cover (580) may be attached by an adhesive, such as cyanoacrylate or epoxy, or alternatively by heat sealing. While a certain materials and attachment methods for second cover (580) have been described herein, various other materials and attachment methods for second cover (580) will be apparent to those of ordinary skill in the art in view of the teachings herein.

After second cover (580) is attached, the entire package system may be sterilized by a second sterilization method. One such second sterilization method is electron beam sterilization for surface sterilization, though it should be understood that other sterilization methods may also be employed. Furthermore, while the second sterilization method is described as applying to the entire package system, the second sterilization method may be applied to only to the surface of the insertable electrical component (560). Alternatively, each component herein described may be individually sterilized prior to packaging. Various other suitable sterilization methods that may be provided will be apparent to those of ordinary skill in the art in view of the teachings herein.

With the package system assembled, insertion assembly (500) is shown in a ready-to-use state in FIG. 6A. While insertion assembly (500) has been described for one exemplary configuration, it will be apparent to one of ordinary skill in the art in view of the teachings herein that insertion assembly (500) may be implemented on other configurations for package systems, including but not limited to those shown and described in reference to FIGS. 3-5. It should also be understood that multiple insertion assemblies (500) may also be implemented for multi-compartment package systems as well.

In the present example, insertable electrical component (560) and medical device (550) are substantially aligned along a common axis. When medical device (550) is to be used, pull tab (540) is pulled in a direction substantially transverse to that axis in order to separate top portion (532) from first cover (570), as shown in FIG. 6B. Alternatively, first cover (570) may have perforations located near the attachment point of top portion (532) such that a portion of first cover (570) breaks away with top portion (532) when sufficient force is applied when pulling pull tab (540). Once the connection is broken, detachable wall (530) may then be pulled away from first cover (570) to allow communication between first compartment (510) and second compartment (520) while still maintaining a sterile environment within the package system. It should be noted that in the present example first proximal wall (not shown), first bottom surface (412), first distal wall (414), second proximal wall (426), second bottom surface (422), and second distal wall (424) form a single homogeneous continuous length of flexible material. In the present example, with top portion (532) detached from first cover (570), first distal wall (514) and second proximal wall (526) are still intact such that the sterility of both first compartment (510) and second compartment (520) is maintained. Other suitable ways to detach detachable wall (530) from first cover (570) will be apparent to those of ordinary skill in the art in view of the teachings herein.

As shown in FIG. 6C, a user may then push on second distal wall (524) to push insertable electrical component (560) into medical device (550). Second distal wall (524) of the present example comprises a flexible wall (528) having excess flexible material to allow a user to more easily push insertable electrical component (560) into medical device (550). Flexible wall (528) may simply comprise a bulge or a semi-spherical bubble of excess flexible material or flexible wall (528) may comprise a plurality of concentric rings that expand in an accordion-like manner. Other suitable flexible wall portions (528) will be apparent to those of ordinary skill in the art in view of the teachings herein.

Once the insertable electrical component (560) is attached to or inserted into medical device (550), second cover (580) and first cover (570) are removed and medical device (550) is used.

While insertion assembly (500) has been described in reference to a certain exemplary package system configuration, other implementations of insertion assembly (500) will be apparent to those of ordinary skill in the art in view of the teachings herein. Such implementations may include use with the various package systems disclosed herein or the use of multiple insertion assemblies (500) within a single package system.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in a variety of fields, including, but not limited to, conventional medical instrumentation and open surgical instrumentation as well as robotic-assisted surgery.

Having shown and described various embodiments of the present invention, further adaptations of the methods and systems described herein may be accomplished by appropriate modifications by one of ordinary skill in the art in view of the teachings herein without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for aseptic attachment or insertion of an insertable electrical component comprising:
    (a) a container, wherein the container is sized and configured to receive a medical device, wherein the container comprises a first compartment, a second compartment, and a detachable wall, wherein the detachable wall is connected to the first compartment and the second compartment, wherein the detachable wall is disposed between the first compartment and the second compartment;
    (b) a first cover, wherein the first cover is movable from a first position where the first cover is removably attached to the first compartment such that the first cover effectively seals the first compartment to a second position where the first cover no longer effectively seals the first compartment; and
    (c) a second cover, wherein the second cover is movable from a first position where the second cover is removably attached to and covers a portion of the container to a second position where the second cover no longer covers the portion of the container;
    wherein the detachable wall is removably attached to the first cover;
    wherein one or both of the first cover or the second cover are configured to cooperate with the container in a manner sufficient to maintain sterility of a medical device within the container;

wherein the second cover covers the first compartment and the second compartment when the second cover is in the first position, thereby preventing access to the first cover.

2. The apparatus of claim 1, wherein the detachable wall is defined by a top portion, a portion of a first distal wall of the first compartment, and a portion of a second proximal wall of the second compartment, wherein the top portion of the detachable wall is removably attached to the first cover.

3. The apparatus of claim 2, wherein the top portion of the detachable wall is attached to the first cover by an adhesive.

4. The apparatus of claim 2, wherein the first cover comprises a plurality of perforations parallel to the top portion and located proximal to the top portion.

5. The apparatus of claim 2, further comprising a pull tab secured to the detachable wall.

6. The apparatus of claim 1, wherein the first compartment, second compartment, and detachable wall are made of a flexible material.

7. The apparatus of claim 6, wherein the second compartment has a second distal wall, wherein the second distal wall comprises a flexible wall portion.

8. The apparatus of claim 7, wherein the flexible wall portion comprises a semi-spherical bubble of flexible material.

9. The apparatus of claim 7, wherein the flexible wall portion comprises a plurality of concentric rings of flexible material formed in an accordion fold configuration.

10. The apparatus of claim 1, further comprising a medical device contained within the first compartment and an insertable electrical component contained within the second compartment.

11. The apparatus of claim 10, wherein the insertable electrical component comprises a power source.

12. The apparatus of claim 1, wherein the container further comprises a perimeter rim, and wherein the second cover comprises a peelable film adhesively attached to the perimeter rim.

13. The apparatus of claim 12, wherein the peelable film is adhesively attached to a portion of the first cover and to a portion of the perimeter rim.

14. The apparatus of claim 1, wherein the container is a blister tray, wherein the blister tray is formed of a single homogeneous continuous material.

15. An apparatus for aseptic attachment or insertion of an insertable electrical component comprising:
(a) a container, wherein the container is sized and configured to receive a medical device, wherein the container comprises a first compartment, a second compartment, and a detachable wall, wherein the detachable wall is connected to the first compartment and the second compartment, wherein the detachable wall is disposed between the first compartment and the second compartment;

(b) a first cover, wherein the first cover is movable from a first position where the first cover is removably attached to and covers the first compartment to a second position where the first cover no longer covers the first compartment; and (c) a second cover, wherein the second cover is movable from a first position, where the second cover is removably attached to and covers the first and second compartments, to a second position, where the second cover no longer covers the first and second compartments;

wherein the detachable wall is removably attached to the first cover;

wherein one or both of the first cover or the second cover are configured to cooperate with the container in a manner sufficient to maintain sterility of a medical device within the container;

wherein the top portion of the detachable wall is attached to the first cover by an adhesive.

16. An apparatus for aseptic attachment or insertion of an insertable electrical component comprising:
(a) a container, wherein the container is sized and configured to receive a medical device, wherein the container comprises a first compartment, a second compartment, and a detachable wall, wherein the detachable wall comprises a flexible material and is defined by a first wall of the first compartment, a second wall of the second compartment, and a third wall extending between the first wall and second wall;

(b) a first cover, wherein the first cover is movable from a first position where the first cover is removably attached to and covers the first compartment to a second position where the first cover no longer covers the first compartment;

(c) a second cover, wherein the second cover is movable from a first position where the second cover is removably attached to and covers a portion of the container to a second position where the second cover no longer covers the portion of the container; and (d) a pull tab secured to a first side of the third wall;

wherein a second side of the third wall is removably attached to the first cover;

wherein one or both of the first cover or the second cover are configured to cooperate with the container in a manner sufficient to maintain sterility of a medical device within the container;

wherein the first cover and second cover are spaced from one another in their respective first positions.

17. The apparatus of claim 16, wherein the second cover is sized and configured to removably attach only to the second compartment of the container.

* * * * *